United States Patent
Markwort et al.

(10) Patent No.: US 8,460,946 B2
(45) Date of Patent: Jun. 11, 2013

(54) METHODS OF PROCESSING AND INSPECTING SEMICONDUCTOR SUBSTRATES

(75) Inventors: Lars Markwort, Haimhausen (DE); Pierre-Yves Guittet, Munich (DE); Sandip Halder, Leuven (BE); Anne Jourdain, Leuven (BE)

(73) Assignees: Nanda Technologies GmbH, Unterschleissheim (DE); IMEC, Leuven (BE)

( * ) Notice: Subject to any disclaimer, the term of this patent is extended or adjusted under 35 U.S.C. 154(b) by 0 days.

(21) Appl. No.: 13/089,127

(22) Filed: Apr. 18, 2011

(65) Prior Publication Data

US 2012/0094401 A1   Apr. 19, 2012

(30) Foreign Application Priority Data

Apr. 19, 2010   (EP) ...................................... 10004141

(51) Int. Cl.
*H01L 21/00* (2006.01)
(52) U.S. Cl.
USPC ..................................... 438/16; 257/E21.576
(58) Field of Classification Search
USPC ........................................................... 438/16
See application file for complete search history.

(56) References Cited

U.S. PATENT DOCUMENTS

| | | | |
|---|---|---|---|
| 4,933,567 A | 6/1990 | Silva et al. | |
| 6,916,725 B2 | 7/2005 | Yamaguchi | |
| 7,115,858 B1 | 10/2006 | Holden et al. | |
| 7,214,615 B2 | 5/2007 | Miyazawa | |
| 7,851,923 B2 * | 12/2010 | Erturk et al. | 257/773 |
| 2002/0182760 A1 * | 12/2002 | Wack et al. | 438/14 |
| 2003/0218753 A1 * | 11/2003 | Reuter | 356/445 |
| 2005/0158889 A1 | 7/2005 | Brouillette et al. | |
| 2007/0275543 A1 * | 11/2007 | Abe et al. | 438/464 |
| 2009/0008794 A1 | 1/2009 | Wu et al. | |
| 2009/0227047 A1 | 9/2009 | Yang et al. | |
| 2010/0032764 A1 | 2/2010 | Andry et al. | |
| 2010/0038800 A1 | 2/2010 | Yoon et al. | |
| 2010/0041226 A1 | 2/2010 | Reid et al. | |

FOREIGN PATENT DOCUMENTS

WO   WO 2009/121628 A2   10/2009

OTHER PUBLICATIONS

Jordain A. et al., "New Hybrid Bonding Approach for 3D Stacking of ICs", Chip Scale Review, Aug./Sep. 2009, pp. 24-28.
Markwort L. et al., "Full wafer CD-imaging for excursion control of fast patterning processes", SPIE 2010/7638-6, pp. 1-24.
Swinnen B., "TSV Metrology and Inspection Challenges for 3D-Integration", IMEC 2009, pp. 1-27, Semicon West 2009, San Francisco, USA Jul. 14-16, 2009.
Teixeira R. et al., "Stress Analysis on Ultra Thin Ground Wafers", Journal Integrated Circuits and Systems 2008, v.3 / n.2:81-87.
Yeo et al., "Sensitivity improvement and noise reduction of array CD mapping on memory device using inspection tool", Proc. of SPIE vol. 7272 72721U-1, 2009.
European Search Report dated Aug. 10, 2010 from corresponding application No. EP 10 004 141.7.
International Search Report and Written Opinion mailed on Jul. 4, 2011 for PCT Application No. PCT/EP2011/001992 filed on Apr. 19, 2011, 14 pages.

* cited by examiner

*Primary Examiner* — William D Coleman
(74) *Attorney, Agent, or Firm* — Silicon Valley Patent Group LLP

(57) ABSTRACT

A method of inspecting a semiconductor substrate having a back surface and including at least one piece of metal embedded in the substrate comprises directing measuring light towards the back surface of the substrate and detecting a portion of the measuring light received back from the substrate. The method also includes determining a distance between the piece of metal and the back surface based upon the detected measuring light received back from the substrate.

20 Claims, 6 Drawing Sheets

METHODS OF PROCESSING AND INSPECTING SEMICONDUCTOR SUBSTRATES

CROSS-REFERENCES TO RELATED APPLICATIONS

The present application claims priority to European Patent Application No. EP 10 004 141.7, filed Apr. 19, 2010. The disclosure of which is hereby incorporated by reference in its entirety.

TECHNICAL FIELD

The invention relates to methods of inspecting semiconductor substrates and to methods of processing semiconductor substrates. The invention also relates to methods of manufacturing semiconductor devices and to devices manufactured using such methods.

BACKGROUND OF THE INVENTION

A semiconductor wafer substrate generally includes a front side having integrated circuits formed thereon, and a bulk of semiconductor material providing the back side of substrate. Prior to bonding and packaging of individual integrated circuit chips or bonding to other semiconductor substrates, the wafer substrate is typically thinned to remove unwanted semiconductor material or to expose through wafer vias embedded in the substrate to provide electrical contact from the back side to the integrated circuits formed on the front side.

It is desirable to perform the thinning of the wafer with a high accuracy which is uniform across the wafer such that a remaining thickness of the wafer has a desired value or such that a residual thickness measured between tip ends of the through wafer vias embedded in the substrate and the back surface of the wafer has a desired value.

BRIEF SUMMARY OF THE INVENTION

The present invention has been accomplished taking the above problems into consideration.

According to embodiments of the present invention, the processing of semiconductor substrates includes optical methods to determine a distance between a piece of metal embedded in a semiconductor substrate and a back surface of the substrate.

According to other embodiments, optical methods are used to detect pieces of metal embedded in the substrate and not exposed at the back surface of the substrate and to control a wafer thinning process based on such detection.

According to particular embodiments herein, information gained by the optical methods from one wafer can be used to control a subsequent thinning process applied to the same wafer or to control a thinning process applied to a next wafer.

According to other particular embodiments herein, other information, such as information relating to grinding marks detected on the back surface, can be used to control a subsequent grinding process applied to a next wafer.

According to exemplary embodiments, the optical methods include directing measuring light towards the back surface of the substrate and detecting a portion of the measuring light received back from the substrate. According to exemplary embodiments herein, the direction of measuring light towards the back surface and the detection of the portion of measuring light received back from the substrate uses a dark field configuration. A minimum angle between a direction of a portion of the measuring light reflected off the back surface and a direction of the portion of the measuring light received back from the substrate is greater than 10°, greater than 20° or greater than 30°. The inventors have found that a dark field configuration which is conventionally used to detect defects, such as particles or scratches, on a substrate surface can be successfully applied to detect features embedded in the bulk of the substrate. Such features may comprise pieces of metal embedded in a substrate made of semiconductor material.

According to embodiments, the optical methods comprise imaging of a portion of the substrate onto a position sensitive detector. According to exemplary embodiments herein, a lateral extension of the feature embedded in the bulk of the substrate is at least 2 times smaller or at least 5 times smaller than a lateral resolution of the imaging of the portion of the substrate onto the position sensitive detector. According to other exemplary embodiments herein, a lateral extension of a region of a substrate imaged onto one single pixel of a position sensitive detector is at least ten times greater or at least 20 times greater than a lateral extension of the features embedded in the substrate.

According to other embodiments, the optical methods include directing of a measuring light beam onto the substrate such that a lateral extension of the beam of measuring light on the back surface is at least 2 times greater, at least 5 times, at least 10 times, or at least 100 times greater than a lateral extension of the feature embedded in the substrate. Herein, the beam of measuring light can be scanned across the substrate to generate an image of the substrate and to perform the optical methods at plural locations of the substrate.

According to embodiments, measuring light used in the optical methods has wavelengths selected such that a penetration depth of the measuring light into the substrate material is greater than 0.2 times, 0.5 times or 1.5 times a distance between features embedded in the substrate and the back surface of the substrate. According to exemplary embodiments herein, the substrate material is silicon, and the wavelengths of the measuring light are greater than 500 nm, 550 nm, 600 nm or 650 nm.

According to exemplary embodiments, wavelengths of measuring light used in the optical methods are selected such that a penetration depth of the measuring light into the substrate is less than 2.0 times, 1.0 times or 0.5 times a distance between the back surface of the substrate and a front surface of the substrate opposite to the back surface. According to exemplary embodiments herein, the substrate material is silicon, and the wavelengths of the measuring light are smaller than 900 nm, 850 nm, 800 nm or 750 nm.

According to exemplary embodiments, the pieces of metal embedded in the substrate material are through wafer vias, i.e. conductive connectors extending from a front side of the substrate into the substrate.

According to embodiments, a thinning process is applied to a back side of the substrate to remove substrate material. According to exemplary embodiments herein, the thinning process comprises grinding and/or etching. The thinning process may be controlled based on information gained in one of the optical methods disclosed in this application.

According to embodiments, a method of manufacturing a semiconductor device is provided, wherein the method comprises forming semiconductor structures and through wafer vias on a front side of a first semiconductor substrate, bonding the first substrate with its front side to a carrier, applying at least one thinning process to the first substrate by removing substrate material at a back side of the substrate such that the through wafer vias are exposed at the back side, and bonding at least one second substrate to the first substrate, wherein the at least one thinning process is controlled based on information gained from one of the optical methods illustrated above.

BRIEF DESCRIPTION OF THE DRAWINGS

The forgoing as well as other advantageous features of the invention will be more apparent from the following detailed description of exemplary embodiments of the invention with reference to the accompanying drawings. It is noted that not all possible embodiments of the present invention necessarily exhibit each and every, or any, of the advantages identified herein.

DETAILED DESCRIPTION OF THE INVENTION

Figure 1:
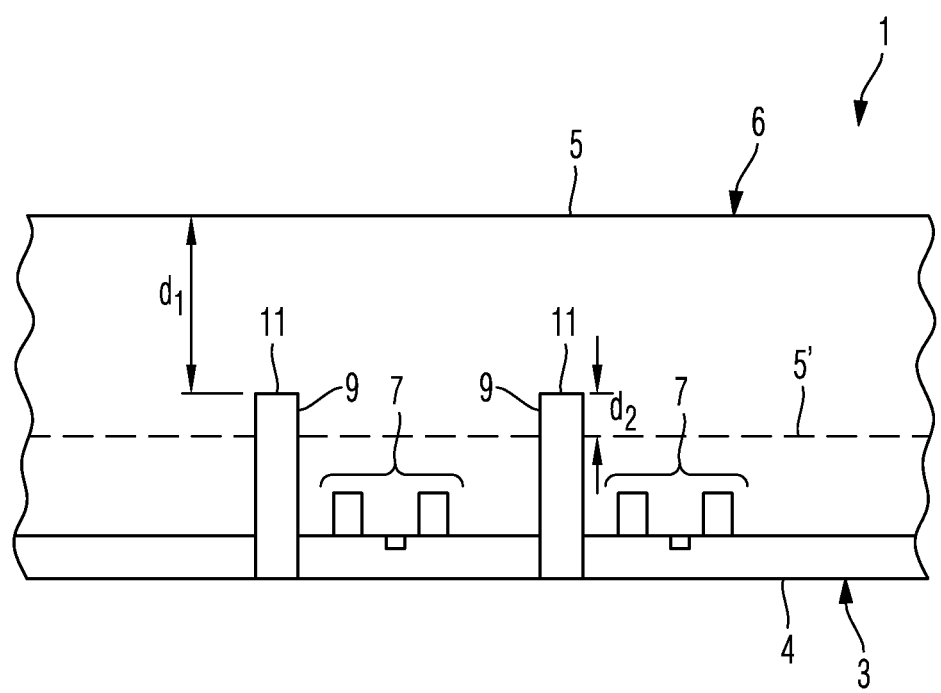
FIG. 1 is a schematic illustration of a cross section of a wafer substrate having through wafer vias embedded therein.

In the exemplary embodiments described below, components that are alike in function and structure are designated as far as possible by alike reference numerals. Therefore, to understand the features of the individual components of a specific embodiment, the descriptions of other embodiments and of the summary of the invention should be referred to.

The embodiments illustrated below generally relate to manufacture of semiconductor devices and to thinning of wafers and in particular to thinning of such wafers including through wafer vias which are to be exposed at a back side of the wafer by applying a thinning process to the back side of the wafer. Background information relating to thinning of wafers and to wafers including through wafer vias can be obtained from U.S. Pat. No. 7,214,615 B2, U.S. Pat. No. 6,916,725 B2, US 2010/0038800 A1, US 2010/0032764 A1, US 2005/0158889 A1 and US 2010/0041226 A1, wherein the full disclosure of these documents is incorporated herein by reference.

Further information to manufacture of semiconductor devices involving thinning of a wafer can be obtained from the article "Stress Analysis on Ultra Thin Ground Wafers" by Ricardo C. Teixeira et al., Journal Integrated Circuits and Systems 2008, v.3/n.2:81-87 and from the article "New Hybrid Bonding Approach for 3D Stacking of ICs" by Anne Jourdain et al., Chip Scale Review, August/September 2009, pages 24 to 28.

The illustrated embodiments relate to thinning of wafers and involve optical methods used for determining a residual thickness between tip ends of through wafer vias and a back surface of a wafer and for obtaining information which can be used for controlling a thinning process. These optical methods are, however, not limited to those applications. The optical methods can be also applied to other substrates in which features are embedded in the substrate such that they are located below a surface of the substrate.

FIG. 1 is a schematic illustration of a cross section of a semiconductor wafer in a manufacturing process for semiconductor devices. The wafer 1 has a front surface 6 at a front side 3 and a back surface 5 at a back side 4. A plurality of semiconductor devices 7, such as field effect transistors, are formed at the front side 3 of the wafer 1 by applying a plurality of lithographic steps and other manufacturing steps to the front side 3 of the wafer 1. Through wafer vias 9 extend from the front side 3 into the substrate material of the wafer 1. The through wafer vias 9 can be formed by conventional methods, such as etching trenches into the substrate, depositing insulating material on trench walls and filling the trenches with a conductive material, such as copper. The through wafer vias have a high aspect ratio and extend into the substrate of the wafer such that tip ends 11 of the through wafer vias 9 are located at a residual distance $d_1$ from back surface 5 of the wafer 1. Exemplary values of the residual distance $d_1$ after manufacture of the through wafer vias 9 include 630 μm and 730 μm, depending on a thickness of the wafer 1.

One or more wafer thinning processes will be applied to the wafer 1 schematically illustrated in FIG. 1 to expose the vias 9 at the back surface of the wafer. The thinning process includes removal of substrate material from the back surface 5 of the wafer 1.

A broken line 5' in FIG. 1 illustrates a position of the back surface of the wafer after thinning such that the vias 9 are exposed and project a distance $d_2$ from the surface. Exemplary values of the distance $d_2$ are 1 μm and 2 μm, for example. It is apparent that the thinning process has to be performed with a high accuracy to maintain the achieved distances $d_2$ within an acceptable range for all the vias 9 distributed across the substrate 1. Therefore, it is desirable to control the one or more thinning processes based on measurements. A conventional optical measurement to control wafer thinning is known from US 2005/0158889 A1 and measures a distance between the back surface 5 and the front surface 4 of the wafer. This conventional optical measurement method uses infrared light having a penetration depth in the wafer material which is greater than the distance between the front and back surfaces. Problems in the conventional method may occur if it is not possible to precisely detect the front surface of the wafer due to a presence of a carrier substrate onto which the wafer is attached with its front side 3, and if a depth by which the vias extend into the substrate is not exactly known or not uniform across the wafer.

Therefore, it is desirable to determine the residual distance $d_1$ between tip ends 11 and the back surface 6 of the wafer 1 directly, or to at least determine reliable information indicative of the residual distance $d_1$. For example, if a predefined threshold residual distance of, for example, 5 μm or 10 μm is reached by applying a grinding method, the thinning process can be continued by applying etching until the tip ends are fully exposed.

Figure 2:
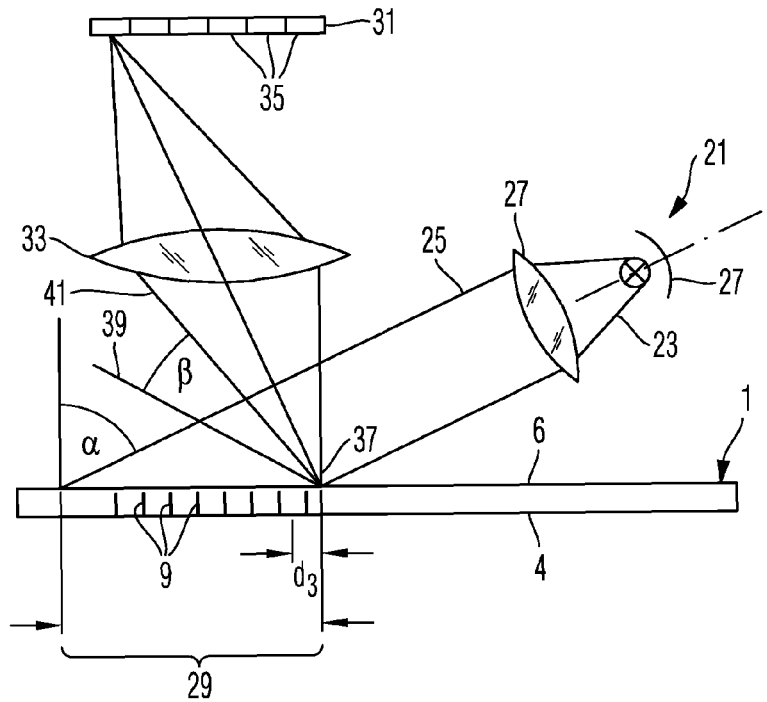
FIG. 2 is a schematic illustration of an optical method.

FIG. 2 is a schematic illustration of an optical configuration which can be used to perform an optical method for determining the residual thickness $d_1$ of the wafer 1 schematically illustrated in FIG. 1. The optical configuration includes a light source 21 to generate measuring light 23 from which a beam 25 of measuring light is shaped by optics 27. The optics 27 may include one or more lenses and one or more mirrors. The beam 25 is directed onto a portion 29 of the back surface 5 of the wafer 1 under an angle α relative to a surface normal which is greater than, for example, 10°, 20° or 30°.

Figure 5:
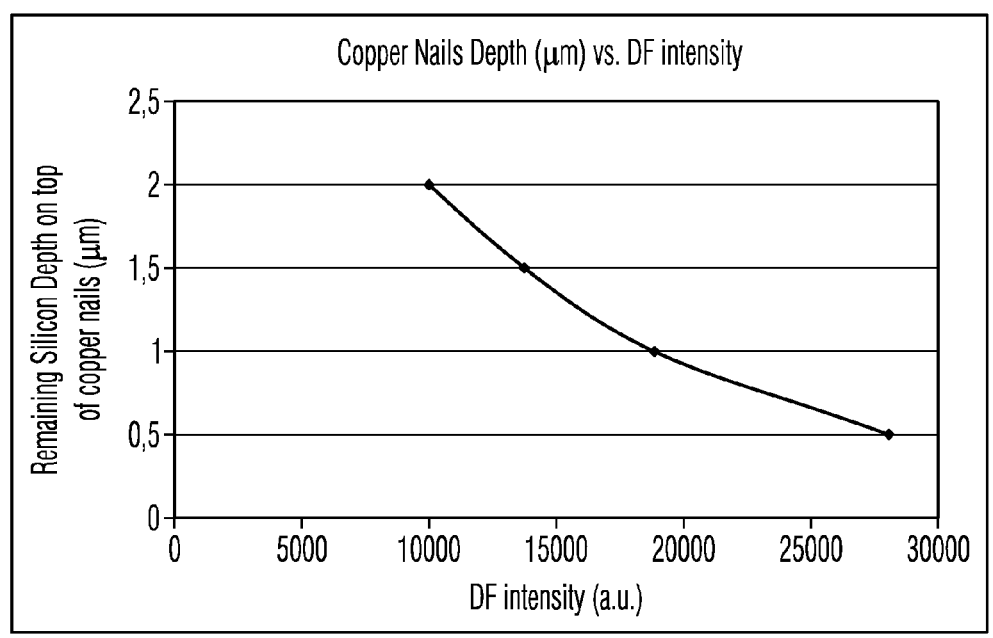
FIG. 5 is a graph illustrating a dependency of a residual depth and image intensity.

The portion 29 of the back surface 5 of the wafer is imaged onto a position sensitive detector 31 using imaging optics 33. The imaging optics 33 may include one or more lenses and one or more mirrors. The position sensitive detector 31 comprises an array of pixels 35. The position sensitive detector 31 may have a high number of pixels, such as 10,000 or more pixels, wherein a number of only six pixels 35 is shown in FIG. 5 for illustrative purposes. Due to the imaging with imaging optics 33, there is a one-to-one correspondence between regions on the wafer 1 and individual pixels onto which each region is imaged. Reference numeral 37 indicates an exemplary region on the substrate 1 which is imaged onto the left pixel 35 of detector 31 shown in FIG. 2. A lateral extension $d_3$ of the region 37 imaged onto the one pixel 35 is, for example, 100 μm. This lateral extension is greater than the lateral extension of the vias 9 embedded in the substrate. An exemplary value of the lateral extension of a via 9 is 2 μm to 20 μm.

The optical configuration illustrated in FIG. 2 is a dark field configuration as illustrated by an angle β shown in FIG. 2. The angle β is a minimum angle between rays 39 of measuring light 25 specularly reflected at the back surface 5 of the wafer and rays 41 of the portion of the measuring light scattered at the wafer 1 and received by the detector 31. This minimum angle β is greater than 10°, 20° or 30°, for example.

Wavelengths of the light of the measuring beam 25 are selected to fulfil certain requirements illustrated below in more detail. For this purpose, transmissive filters allowing only certain wavelengths to traverse or reflective filters reflecting only certain wavelengths can be disposed in the beam path of the measuring light beam 25. A same result can be achieved if the measuring light beam 25 includes a generally broad spectrum of wavelengths and wherein a wavelength selection is performed in the imaging beam path between the substrate 1 and the detector 31 by providing suitable transmissive or reflective filters. Moreover, the light source 21 can be configured such that it generates substantially only light from a desired wavelength range.

The portion 29 which is imaged onto the detector 31 may have a lateral extension such that plural through wafer vias 9 are located within the region 29. The number of vias located within the region 29 may exceed 100 vias or many thousand vias. Still further, the lateral extension of the region 29 can be greater than a lateral extension of dice formed from the wafer 1 later by dicing. For example, the lateral extension of the region 29 can be selected such that it includes more than one, more than two, more than five or even more dice. Moreover, the region 29 imaged onto the detector 31 may include the full wafer 1 such that the lateral extension of the region 29 can be greater than 200 mm or greater than 300 mm depending on the diameter of the wafer 1. An example of an optical configuration which can be used in optical methods illustrated in the present disclosure is illustrated in WO 2009/121628 A2, the full disclosure of which is incorporated herein by reference.

Figure 3:
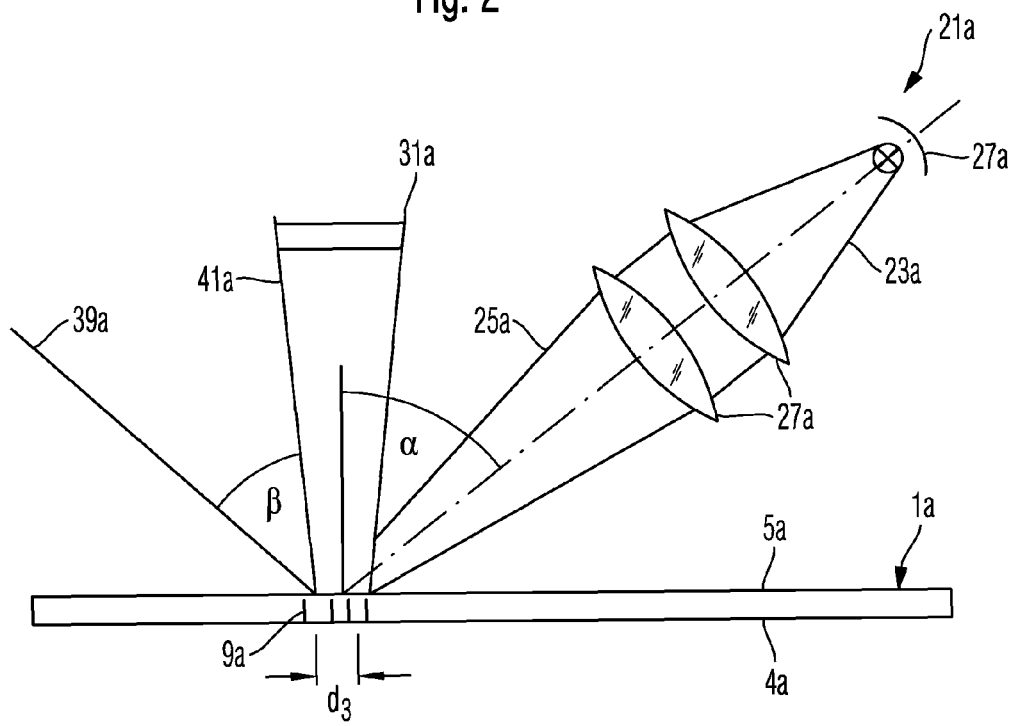
FIG. 3 is a schematic illustration of another optical method.

An alternative optical configuration which can be used in the optical methods illustrated in this disclosure is schematically shown in FIG. 3. This setup includes a light source 21a generating measuring light 23a which is shaped to a focussed beam 25a of measuring light by optics 27a which may comprise one or more lenses and one or more mirrors. The focused beam 25a of measuring light is directed onto a back surface 5a of a wafer 1a such that a lateral extension $d_3$ of the beam 25 at the back surface 5a is greater than a lateral extension of through wafer vias 9a embedded in the wafer substrate. For example, the lateral extension $d_3$ can be 2 times greater, 5 times greater, 10 times greater or even 100 times greater than the lateral extension of the through wafer vias 9a.

The beam of measuring light 25a is directed onto the substrate 1a under an angle α relative to a surface normal of the wafer 1a.

A detector 31a is positioned such that a minimum angle β of rays 39a of measuring light 25a specularly reflected at the back surface 6a of the wafer and rays 41a of the measuring light received by the detector 31a is greater than 10°, 20° or 30°, for example.

The detector 31a may include one single light sensitive element or a number of light sensitive elements. While it is possible that the detector 31a is a position sensitive detector, this is not necessary in the illustrated configuration. An image of the wafer 1a can be obtained by scanning the beam 25a across the back surface 5a of the wafer and recording light intensities detected with the detector 31a in dependence of a position to which the beam 25a is directed. For example, the wafer 1a can be rotated and/or otherwise displaced relative to the beam 25a of incident measuring light.

The optical configurations illustrated above with reference to FIGS. 2 and 3 are dark field configurations in which a main direction of measuring light originating from the wafer and received by the detector is oriented substantially parallel to a surface normal of the wafer. It is, however, possible to achieve dark field configurations also with optics in which the light originating from the wafer and received by the detector has a main direction oriented under an angle relative to the surface normal. It is, in particular, also possible to direct the incident measuring light substantially orthogonal onto the wafer surface. The dark field configuration is achieved by the minimum angle between rays of specularly reflected light and rays of detected light. The minimum angle β is in particular greater than 0° and preferable greater than 10°, 20° or 30° for example.

Other configurations of optics which can be used in the optical methods disclosed herein include bright field optical configurations in which there is an angular overlap between rays of measuring light specularly reflected off the surface of the wafer and rays received by a detector.

The inventors have found that optical configurations which are conventionally used for inspection of defects located on a surface of a substrate can also be used for detection of features embedded in the substrate and located at a residual distance from the surface of the substrate.

Figure 4A:
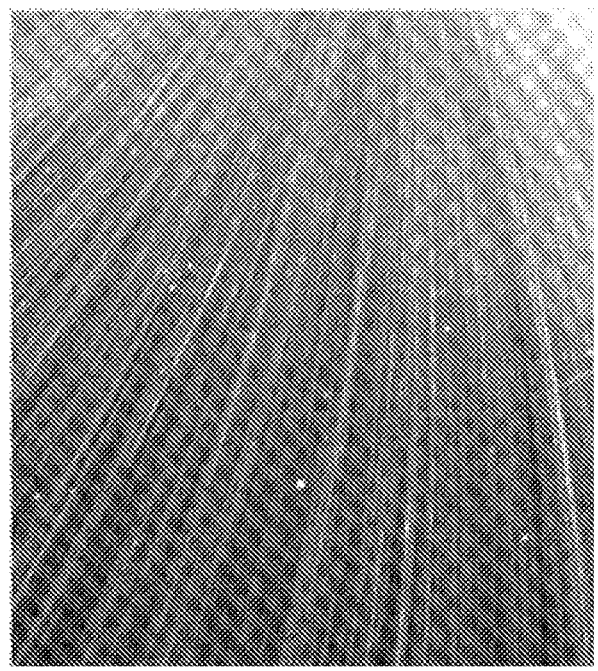
FIGS. 4a, 4b and 4c are images obtained by the optical method illustrated in FIG. 2 at different residual depths of a substrate.
Figure 4B:
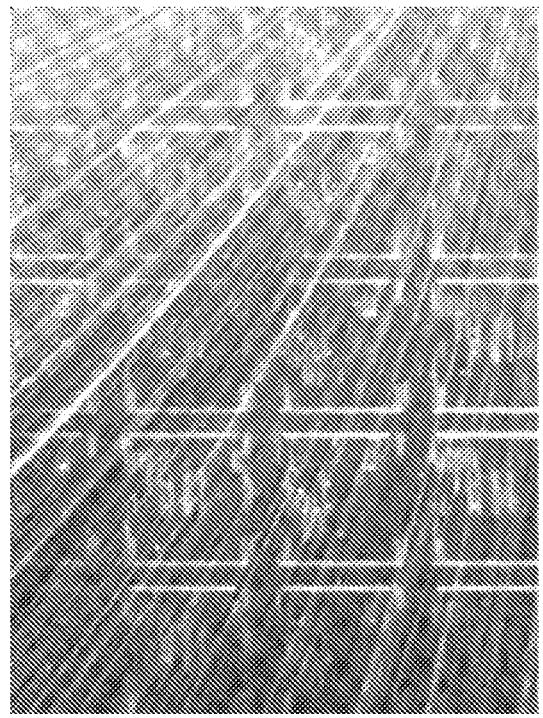
Figure 4C:
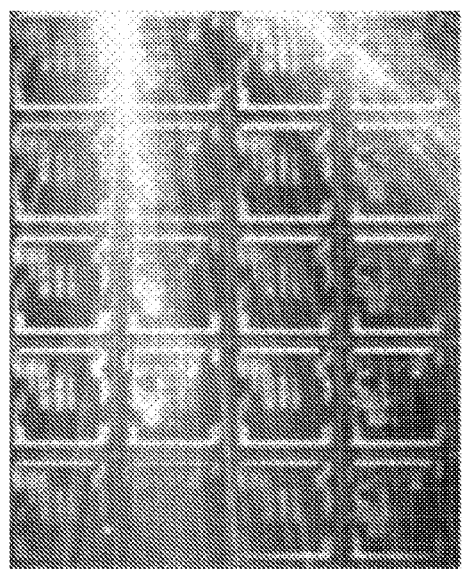

FIGS. 4a, 4b and 4c show images obtained from a back side of a semiconductor wafer having embedded features. The substrate material of the semiconductor wafer is silicon, and the embedded features are through wafer vias made of copper. The three images shown in FIG. 4 are obtained at different residual distances of tip ends of the vias from the back surface of the wafer. In FIG. 4a, the residual distance $d_1$ is 6 μm, and the features visible in the image mostly relate to grinding marks of a grinding tool used in the wafer thinning process. A number of image features which might be indicative of the presence of the through wafer vias is low.

FIG. 4b shows an image of a wafer back side where the residual distance d1 varies between 1 μm and 2 μm. The features visible in the image include grinding marks similar to those of FIG. 4a, and patterns having a structure corresponding to an arrangement pattern of through wafer vias manufactured in the substrate. The features of the grinding pattern and the features of the via pattern are provided in the image with a similar contrast.

FIG. 4c shows an image of the back side of the wafer in which the residual distance $d_1$ of the vias is less than or equal to 0.5 μm. It is apparent that the features corresponding to the arrangement of vias is even more prominent than in FIG. 4b and that the features corresponding to the arrangement of vias have a higher contrast in the image than the features related to the grinding pattern.

From FIGS. 4a, 4b and 4c it is apparent that an image contrast and/or image intensity of patterns contained in an image of a back side of a wafer is indicative of a residual distance between features embedded in the wafer and the back surface of the wafer.

The image contrast produced by features embedded in the substrate and located below the substrate surface can be enhanced by imposing restrictions to the measuring light used for the imaging. For example, it is desirable that light reflected at the front surface of the substrate or light scattered at structures provided on the front side of the substrate do not contribute to the detected image. Such light travels through the substrate material along a path having a length which is at least two times greater than the thickness of the substrate. Therefore, it is advantageous to select wavelengths of the measuring light contributing to the detected image such that a substantial extinction of measuring light occurs after a path length within the material greater than two times the thickness of the substrate. This can be achieved by selecting the wavelengths such that a penetration depth of the measuring light in the substrate material is smaller than 2.0 times, 1.0 times or 0.5 times a thickness of the substrate. In this context, the penetration depth is defined as the depth at which the intensity of the measuring light inside the substrate material falls to $1/e$ (about 37%) of the original value at the surface.

For example, if the substrate material is silicon and a thickness of the substrate can be as small as 10 μm, it is advantageous to use measuring light of wavelengths less than 900 nm, 850 nm, 800 nm or 750 nm, for example.

On the other hand, the measuring light used for generating an image of an arrangement pattern of features located below a back surface of a substrate should still have a significant intensity when it reaches the buried features. Therefore, it is advantageous to select the wavelengths of the measuring light such that a penetration depth of the measuring light in the substrate is greater than 0.2 times, greater than 0.5 times or greater than 1.5 times a residual distance between the buried features and the substrate surface.

In the example where the substrate material is silicon and where the buried features are through wafer vias made of metal, it is advantageous to use measuring light having wavelengths greater than 500 nm, greater than 550 nm, greater than 600 nm or even greater than 650 nm.

Figure 6:
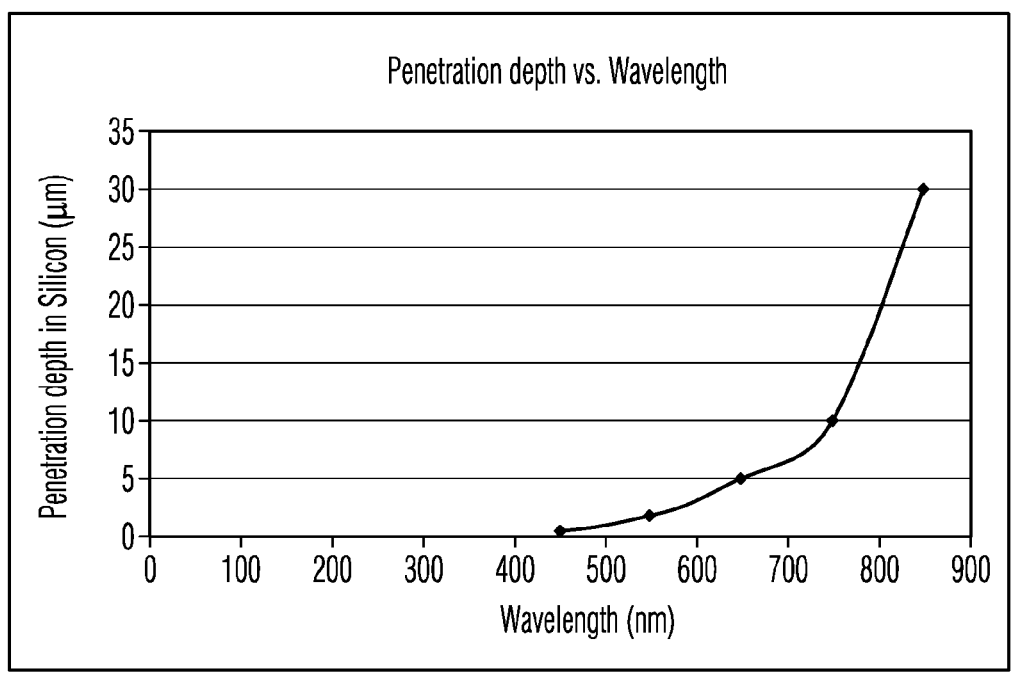
FIG. 6 is a graph showing a dependency of a penetration depth of measuring light in a substrate depending on wavelengths.

FIG. 6 shows experimental data of the penetration depth in μm of light in a silicon substrate material in dependence of the wavelength of the light in nm. It is apparent that a lower limit of the wavelength which can be used to detect features more than 1 μm below the surface should be greater than 500 nm, whereas wavelengths below 900 nm should be used to detect such features in a substrate having a thickness below 35 μm.

FIG. 5 is a graph of experimental data showing the dependency of the residual distance of the through wafer vias, as shown in FIG. 4, in dependence of a dark field image intensity of arrangement patterns of the vias in the image. From this graph it is apparent that the dark field image intensity and contrast are well-suited to be indicative of the residual thickness.

Apart from the wavelengths, the measuring light used for detection can also be selected with respect to its polarization such that a high amount of the incident light enters into the substrate and/or such that the suitably polarized light generates a high image intensity or contrast.

Figure 7:
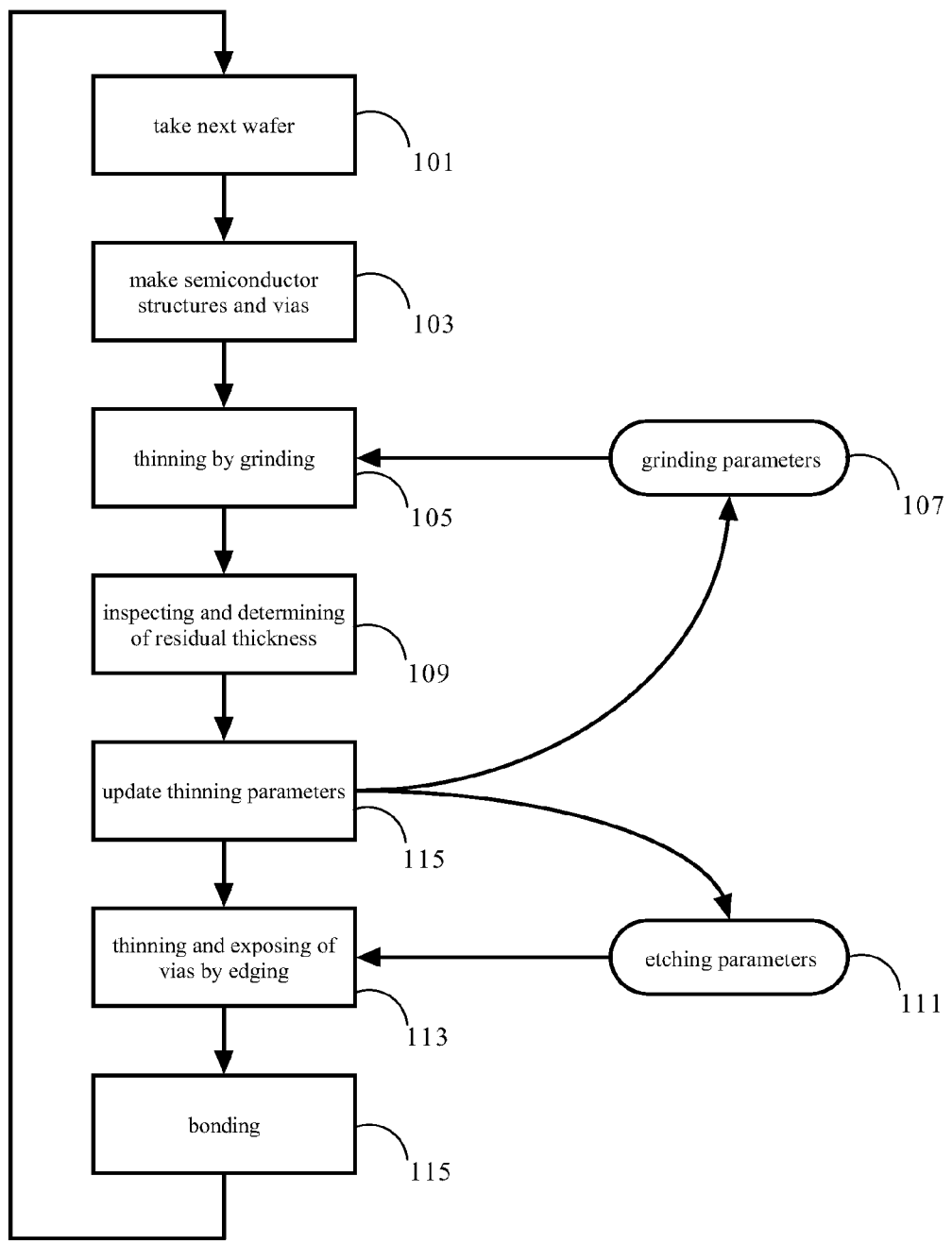
FIG. 7 is a flowchart illustrating a method of manufacturing of a semiconductor device.

The optical methods of inspection of a semiconductor wafer can be used for obtaining information used to control a wafer thinning process in mass production of semiconductor devices. Such manufacturing method is illustrated with reference to the flowchart shown in FIG. 7 below. The method includes bonding a first substrate to a second substrate wherein through wafer vias exposed at a back surface of the first substrate are contacted by the second substrate bonded to the first substrate. In a production of wafers, a next wafer is used for processing in a step 101. Semiconductor structures and vias are formed on a front side of the wafer by lithographic processes and other processes in a step 103. Thereafter, a carrier is attached to a frond side of the wafer, and a thinning process is applied to a back side of the wafer in a step 105. The thinning process may include, for example, grinding and/or polishing. The thinning process is controlled by grinding parameters 107, such as, among others, a number of revolutions per unit time of a grinding or polishing apparatus, a force applied between a grinding or polishing tool and the back side of the wafer or a duration of the grinding or polishing process. The grinding parameters are selected such that a residual thickness between tip ends of the through wafer vias and the back surface of the wafer is 2 μm. Thereafter the residual thickness or information indicative of the residual thickness is determined in a step 109 using optical methods as illustrated above. Based on the determined residual thickness or information indicative of the residual thickness, the control parameters 107 of the thinning process 105 and control parameters 111 of a subsequent thinning process 113 are updated in a step 115. Thereafter, the further thinning process is applied to the back side of the wafer to expose the through wafer vias at the back surface of the wafer in the step 113. Such final thinning process may include an etching which selectively removes substrate material and does substantially not remove the material of the through wafer vias. Also the thinning process of step 113 is controlled by process parameters 111 which may include, among others, a duration of the thinning process, a concentration, composition or temperature of an etching substance, or a plasma intensity applied in the thinning process.

A second substrate is bonded to the wafer in a step 115 after exposing the vias on the back surface. The second substrate may comprise a full wafer or individual dyes of semiconductor devices which have been selected according to suitable quality requirements.

Thereafter, a next wafer is processed at step 101.

It is to be noted that the images obtained from the back surface of the wafer include also other features not related to the through wafer vias. These other features are, for example, generated by defects located on the surface of the substrate. Examples are the grinding marks visible in FIGS. 4a, 4b and 4c. An analysis of such other features can provide information which can be used to control the processing of the wafer. For example the grinding marks can be indicative of a defect of the grinding apparatus used, such that the obtained information may trigger a repair of the grinding apparatus. Moreover, additional images can be obtained in an inspection step by recording one or more images using different wavelengths and polarisations of the measuring light used for imaging.

The information indicative of the residual thickness of the substrate obtained in step 109 can be used to update control parameters of a thinning process applied to the same wafer subsequently. Such process can be referred to as feed-forward control since it is based on information obtained from an individual wafer and is used for controlling further processing of the same wafer. The updating of control parameters of the thinning process applied to the individual wafer in step 105 is a feed-back control since it is effective only for a next wafer processed in a production line.

What is claimed is:

1. A method of processing a semiconductor substrate having a back surface and including at least one piece of metal embedded in the substrate, the method comprising:

determining information indicative of a residual distance between tip ends of the pieces of metal and the back surface of the semiconductor substrate by directing measuring light towards the back surface, wherein determining information indicative of the residual distance further comprises:

detecting and analyzing a portion of the measuring light received back from the pieces of metal embedded in the substrate and having their tip ends disposed at the residual distance from the back surface; and applying a substrate thinning process to the substrate by removing substrate material at the back surface of the substrate, wherein the substrate thinning process applied to the substrate is controlled based upon the determined information indicative of the residual distance.

2. The method according to claim 1 further comprising:
recording an image using the detected measuring light received back from the substrate; and
determining portions of the image corresponding to groups of pieces of metal embedded in the substrate based on predefined arrangement patterns of pieces of metal having a same length embedded in the substrate, wherein the substrate thinning process is controlled based upon the determined portions of the image.

3. The method according to claim 1 wherein a minimum angle between a direction of a portion of the measuring light reflected off the back surface and a direction of the portion of the measuring light received back from the substrate is greater than 10°.

4. The method according to claim 1 wherein an angle between a surface normal of the substrate and a direction of incidence of the measuring light directed towards the back surface is greater than 20°.

5. The method according to claim 1 wherein detecting comprises imaging a portion of the substrate onto a position sensitive detector, and wherein a lateral extension of the at least one piece of metal is at least half a lateral resolution of the imaging of the portion of the substrate onto the position sensitive detector.

6. The method according to claim 1 wherein detecting comprises imaging a portion of the substrate onto a position sensitive detector, the position sensitive detector having a plurality of pixels, and wherein a lateral extension of a region of the substrate imaged onto a single pixel of the plurality of pixels is at least twice a lateral extension of the at least one piece of metal.

7. The method according to claim 1 wherein directing measuring light towards the back surface comprises directing a beam of measuring light onto the back surface such that a lateral extension of the beam of measuring light on the back surface is at twice a lateral extension of the at least one piece of metal.

8. The method according to claim 1 wherein a distance between the piece of metal embedded in the substrate and the back surface of the substrate is more than 1 μm.

9. The method according to claim 1 wherein a wavelength of the measuring light is selected such that a penetration depth of the measuring light in the substrate material is greater than 0.2 times a distance between the piece of metal and the back surface of the substrate.

10. The method according to claim 1 wherein the substrate material comprises silicon and wherein a wavelength of the measuring light is greater than 500 nm.

11. The method according to claim 1 wherein a wavelength of the measuring light is selected such that a penetration depth of the measuring light in the substrate material is less than twice a distance between the back surface of the substrate and a front surface of the substrate opposite to the back surface.

12. The method according to claim 1 wherein the substrate comprises silicon and wherein a wavelength of the measuring light is less than 900 nm.

13. The method according to claim 1 wherein the at least one piece of metal comprises at least one through wafer via.

14. The method according to claim 1 wherein the substrate thinning process comprises at least one of grinding, polishing or etching, and wherein the substrate thinning process is applied before detecting the portion of the measuring light received back from the substrate.

15. The method according to claim 1 wherein the substrate thinning process comprises at least one of grinding, polishing or etching, and wherein the substrate thinning process is applied after detecting the portion of the measuring light received back from the substrate.

16. A method of inspecting a semiconductor substrate having a back surface and including at least one piece of metal embedded in the substrate, the method comprising:
directing measuring light towards the back surface of the substrate;
detecting a portion of the measuring light received back from the at least one piece of metal embedded in the substrate, wherein the at least one piece of metal has a tip end disposed at a residual distance from the back surface; and
determining the residual distance between the tip end of the at least one piece of metal and the back surface based upon the detected measuring light received back from the at least one piece of metal embedded in the substrate.

17. The method according to claim 16 wherein the semiconductor substrate comprises silicon and wherein the at least one piece of metal comprises at least one through wafer via.

18. A method of processing semiconductor substrates having a back surface and including at least one piece of metal embedded in the substrate, the method comprising:
applying a substrate thinning process to a first substrate by removing substrate material at the back surface of the first substrate;
determining information indicative of a residual distance between tip ends of the pieces of metal and the back surface of the semiconductor substrate by directing measuring light towards the back surface of the first substrate, wherein determining information indicative of the residual distance further comprises:
detecting and analyzing a portion of the measuring light received back from the pieces of metal embedded in the first substrate and having their tip ends disposed at the residual distance from the back surface; and
applying a substrate thinning process to a second substrate by removing substrate material at the back surface of the second substrate, wherein the substrate thinning process applied to the second substrate is controlled based upon the determined information indicative of the residual distance.

19. The method according to claim 18 wherein the at least one piece of metal comprises at least one through wafer via.

20. A method of manufacturing a semiconductor device, the method comprising:
forming semiconductor structures and through wafer vias on a front side of a first semiconductor substrate;
bonding the first substrate with its front side to a carrier;
determining information indicative of a residual distance between tip ends of the wafer vias and the back surface of the semiconductor substrate by directing measuring light towards a back surface of the first substrate, wherein determining information indicative of the residual distance further comprises:
detecting and analyzing a portion of the measuring light received back from the wafer vias the first substrate and having their tip ends disposed at the residual distance from the back surface; and
applying at least one thinning process to the first substrate by removing substrate material at the back side of the first substrate such that the through wafer vias are exposed at the back side, wherein the at least one thinning process is controlled based upon the determined information indicative of the residual distance; and
bonding at least one second substrate to the first substrate.

* * * * *